(12) United States Patent
Gohla et al.

(10) Patent No.: US 8,507,276 B2
(45) Date of Patent: *Aug. 13, 2013

(54) TISSUE CULTURE MEDIA USED AS A COMPONENT OF COSMETICS

(75) Inventors: Sven Gohla, Hamburg (DE); Monika Moenks, Schmitten (CH); Sibylle Ibanez, Uetikon am See ZH (CH); Carmen Evangelisti, Freienstein (CH)

(73) Assignee: La Prairie Group AG, Zurich (CH)

( * ) Notice: Subject to any disclaimer, the term of this patent is extended or adjusted under 35 U.S.C. 154(b) by 1218 days.

This patent is subject to a terminal disclaimer.

(21) Appl. No.: 11/285,342

(22) Filed: Nov. 23, 2005

(65) Prior Publication Data

US 2006/0182701 A1    Aug. 17, 2006

Related U.S. Application Data

(63) Continuation of application No. PCT/EP2004/005532, filed on May 22, 2004.

(30) Foreign Application Priority Data

May 24, 2003 (DE) ................... 103 23 510
Nov. 24, 2003 (DE) ................... 103 55 110
Apr. 22, 2004 (DE) .......... 10 2004 020 035

(51) Int. Cl.
*C12N 5/02* (2006.01)

(52) U.S. Cl.
USPC ............. 435/404; 424/78.02; 424/78.03

(58) Field of Classification Search
USPC ............. 435/404; 424/78.02, 78.03
See application file for complete search history.

(56) References Cited

U.S. PATENT DOCUMENTS

| | | | |
|---|---|---|---|
| 4,619,827 A * | 10/1986 | Bull et al. | 424/85.4 |
| 4,708,861 A * | 11/1987 | Popescu et al. | 424/1.21 |
| 4,784,854 A | 11/1988 | Seguin et al. | |
| 5,106,949 A * | 4/1992 | Kemp et al. | 530/356 |
| 5,166,187 A | 11/1992 | Collombel et al. | |
| 5,461,030 A * | 10/1995 | Lindenbaum | 514/4 |
| 5,534,416 A * | 7/1996 | Millard et al. | 436/34 |
| 5,591,709 A * | 1/1997 | Lindenbaum | 514/4 |
| 5,612,040 A * | 3/1997 | Mason et al. | 424/205.1 |
| 5,676,948 A | 10/1997 | Bonte et al. | |
| 5,780,445 A * | 7/1998 | Schneider et al. | 514/27 |
| 5,830,507 A | 11/1998 | Armstrong | |
| 5,834,008 A | 11/1998 | Greenspan | |
| 5,948,385 A * | 9/1999 | Chapman et al. | 424/1.29 |
| 6,150,163 A | 11/2000 | McPherson et al. | |
| 6,372,494 B1 * | 4/2002 | Naughton et al. | 435/391 |
| 6,756,060 B1 | 6/2004 | Greenspan | |
| 2001/0041186 A1 | 11/2001 | Greenspan | |
| 2002/0106703 A1 * | 8/2002 | Sarvetnick et al. | 435/7.21 |
| 2004/0228905 A1 | 11/2004 | Greenspan et al. | |

FOREIGN PATENT DOCUMENTS

| | | |
|---|---|---|
| EP | 0296078 | 12/1988 |
| WO | 98/04681 | 2/1998 |
| WO | 00/15167 | 3/2000 |
| WO | 00/78928 | 12/2000 |
| WO | 01/07605 | 2/2001 |

OTHER PUBLICATIONS http://www.hyclone.com/media/formulations/DMEM HIGH.htm.*
http://www.hyclone.com/media/formulations/DMEM_F12_LM.htm.*
Barnes D., Sato, G. "Methods for Growth of Cultured Cells in Serum-Free Medium" Analytical Biochemistry, vol. 102 (1980), pp. 255-270.
U.S. Appl. No. 10/967,232, filed Oct. 19, 2004 and having the title "Cosmetic or Dermatological Preparation Comprising a Nutrient Medium Phase".
U.S. Appl. No. 11/068,052, filed Mar. 1, 2005 and having the title "Cosmetic or Dermatological Preparation Comprising a Nutrient Medium Phase".

* cited by examiner

*Primary Examiner* — Ruth Davis
(74) *Attorney, Agent, or Firm* — Abel Law Group, LLP

(57) ABSTRACT

A cosmetic or dermatological preparation which comprises one or more tissue culture media, in particular one or more skin cell culture media.

38 Claims, No Drawings

TISSUE CULTURE MEDIA USED AS A COMPONENT OF COSMETICS

CROSS-REFERENCE TO RELATED APPLICATIONS

The present application is a continuation of International Application No. PCT/EP2004/005532, filed May 22, 2004, the entire disclosure whereof is expressly incorporated by reference herein, which claims priority under 35 U.S.C. §119 of German Patent Application Nos. 103 23 510.8, filed May 24, 2003, 103 55 110.7, filed Nov. 24, 2003, and 10 2004 020 035.1, filed Apr. 22, 2004.

BACKGROUND OF THE INVENTION

1. Field of the Invention

The present invention relates to cosmetic or dermatological preparations comprising tissue culture media, in particular skin cell culture media, in particular hydrous serum-free media, and to the use of the preparations for skin care, hair care and body care.

2. Discussion of Background Information

Various circulations exist within the milieu of the human body, such as the blood circulation, the lymphatic system and the intracellular and extracellular tissue fluid. The composition of the solvent water with its mineral and bioorganic constituents in these various "transport media" are the same and are based, highly simplified, on salts, amino acids, vitamins, sugars, proteins and proteids, and trace elements. In the course of evolution, our body has learnt to create within these fluids "communication networks" and nutritional strategies, and an equilibrium of catabolic to anabolic processes, which make the complex life of our multicellular body in fact possible.

If cells are removed from this association, they must be cultivated in "environments" which come as close as possible to the natural living conditions within the body. Requirements for this are supply and transport away of nutrients, and the presence of vital factors.

These environments are known as cell culture media. The mostly liquid medium allows microorganisms or cells to multiply. In principle, the composition of the cell culture medium is dependent on the requirements of the cells to be multiplied. A distinction is made between synthetic media, whose ingredients are accurately known on the basis of pure substances, and complex media, whose exact composition may vary and is in part not accurately known. Cell culture media comprise, besides water, usually a carbon source and a nitrogen source, phosphate compounds and sulfur compounds, and minerals and, where appropriate, growth promoters or vitamins.

If the compositions of the media are suitable, the cells are able to multiply and produce the factors necessary for survival themselves "in situ". By changing the media at suitable intervals it is thus possible to adjust the "steady state" conditions within the tissue.

In order to generate good growth of the cells, sera are frequently added to the cell culture media. Sera are natural products and are obtained from the blood sera of calf, cow, pig, goat, horse, and also from human blood serum. These sera are complex mixtures of various biomolecules, the functionalities of which are tailored to the specific species. They comprise, for example, hormones, adhesion factors, amino acids etc. The individual factors present are variable depending on the origin of the sera sources and thus the batches even of inter-individual sera sometimes vary considerably. Thus, biological experiments can sometimes therefore not be reproduced because the composition of sera used cannot be reproduced by subsequent batches.

In addition, sera are expensive, are only inadequately biologically standardizable and permit no thermal sterilization. In addition, the use of animal sera within products for skin care and dermatology is not indicated since viral impurities are not excluded. Attempts are therefore made to make do with media which contain no sera. The serum-free culture media make it possible to cultivate cells under controlled and defined conditions, so that undesired effects due to variations in the serum composition are eliminated. In addition, contamination of the cell cultures with viruses and bacteria is reduced on use of serum-free media.

It is known that skin cells in particular can be kept alive particularly gently and long-term, and can even be induced to multiply and differentiate in one-, two- and three-dimensional cultures by optimizing the constituents within the culture medium. It has also been possible to demonstrate that suitable media also make the production of growth factors in situ possible, these so-called "conditioned media" being used as growth- or differentiation-promoting cell culture additives.

The keratinized epidermis forms the protective shield of the skin. For this function to be optimally exercised it is necessary for the skin cells (keratinocytes) to pass through the process of so-called epidermal differentiation. After division of the cells in the basal layer, the keratinocytes migrate to the skin surface and undergo a number of changes during this until they form, as dead, flat, anuclear corneocytes, the horny layer (stratum corneum), and finally flake off. During the epidermal differentiation there is formation of various proteins having specific functions. These include, inter alia, keratins, involucrin, filaggrin and transglutaminase. For optimal formation of the epidermis and the horny layer it is necessary for these proteins to be formed in coordinated fashion and in sufficient quantity.

The prior art discloses many cosmetics, skin care preparations or wound-healing preparations which help to compensate or at least reduce the impairments of the skin.

Thus, for example, aging skin is cosmetically treated primarily with vitamin A derivatives or hydroxy acids which lead, via stimulation of the proliferation of the basal cells in the epidermis, to a thickening of the epidermis and thus smoothing of the skin. More recent approaches involve the targeted replacement of the proteins which are absent or in reduced quantity in dry skin or aging skin, or indirect intervention in the metabolic processes which are disturbed in dry skin or with increasing age, in order to normalize them. An example which may be mentioned here is stimulation of collagen synthesis with the aim of reducing wrinkles. In addition, for example, laminin, substances for prolonging the lifetime of skin cells and certain extracts are used for stimulating epidermal differentiation. However, some of these are pharmacologically active substances with a high potential for side effects.

None of the preparations known from the prior art allow the skin to regenerate itself without having a certain degree of harmful side effects or at least undesired side effects. Very often this is because of the high concentrations of the active substances which have to be used in order to achieve the biopharmaceutically effective concentrations at the target organ. At the skin target organ, the skin barrier hinders the dermal effect of active substances. Since changing the skin barrier can result in increased sensitivity of the skin, accompanying skin irritations are not untypical, particularly in the case of dermatology products.

Sensitive skin is often based on disregulation of homeostasis. Here, either lipids or messengers are produced in insufficient amounts, if at all. This leads to reduced intrinsic protection and to increased sensitivity of the skin.

In addition, in the case of skin injuries, such as, for example, burns, the upper layers of the skin are irreversibly destroyed, in which case it must be made possible for the cells which remain to be able to regenerate the healthy tissue association within the shortest time. This requires suitable conditions.

It would be advantageous to be able to improve the supply to the skin of essential, mineral and/or organic biofactors. It would therefore be desirable to provide a cosmetic or dermatological preparation which allows the skin to be able to regenerate itself without the harmful side effects or undesired side effects arising. It would also be desirable to provide preparations which enrich the prior art and can be used for skin care, hair care and body care, and also for the treatment of skin irritations and burns.

SUMMARY OF THE INVENTION

The present invention provides a cosmetic or dermatological preparation which comprises one or more tissue culture media.

In one aspect of the preparation, the one or more tissue culture media may comprise one or more skin cell culture media. These one or more skin cell culture media may be present in a mixture with one or more other tissue culture media.

In another aspect of the preparation, the one or more tissue culture media may be present as a component of the water phase of the preparation in an amount of from 0.1% to 100% by weight, e.g., in an amount of from 1% to 50% by weight, based on the total weight of the preparation.

In yet another aspect, the one or more tissue culture media may comprise the following components in the following concentration ranges in mg/l:

| Biotin | 0.0036 | 0.0146 |
|---|---|---|
| $CaCl_2 \cdot 2H_2O$ | 4.41 | 116.61 |
| Calcium pantothenate | 0.25 | 2.24 |
| Choline chloride | 9 | 13.96 |
| $CuSO_4 \cdot 5H_2O$ | 0.0002496 | 0.00125 |
| D-Glucose | 1081 | 3151 |
| $FeSO_4 \cdot 7 H_2O$ | 0.417 | 1.39 |
| Folic acid | 0.79 | 2.65 |
| Glycine | 7.51 | 18.75 |
| Inositol | 12.6 | 18.02 |
| KCl | 111.83 | 311.8 |
| L-Alanine | 4.5 | 8.91 |
| L-Arginine•HCl | 147.5 | 210.7 |
| L-Asparagine | 7.5 | 15.01 |
| L-Aspartic acid | 3.99 | 6.65 |
| L-Cysteine•HCl | 15.75 | 42.04 |
| L-Glutamine | 365.3 | 877.2 |
| L-Glutamic acid | 7.35 | 14.71 |
| L-Histidine•HCl•$H_2O$ | 16.77 | 31.5 |
| Lipoic acid | 0.11 | 0.2063 |
| L-Isoleucine | 1.968 | 54.5 |
| L-Leucine | 59 | 65.6 |
| L-Lysine•HCl | 18.27 | 91.25 |
| L-Methionine | 4.475 | 17.24 |
| L-Phenylalanine | 4.956 | 35.5 |
| L-Proline | 17.25 | 34.53 |
| L-Serine | 26.25 | 63.06 |
| L-Threonine | 11.91 | 53.5 |
| L-Tyrosine | 2.718 | 38.7 |
| L-Valine | 35.13 | 52.85 |
| $MgCl_2 \cdot 6 H_2O$ | 61 | 122 |

-continued

| $Na_2HPO_4 \cdot 7 H_2O$ | 71 | 536.2 |
|---|---|---|
| NaCl | 6999.5 | 7599 |
| $NaHCO_3$ | 1176 | 2438 |
| Sodium pyruvate | 47 | 63 |
| Nicotinamide | 0.03663 | 2.02 |
| Pyridoxine HCl | 0.031 | 0.06171 |
| Riboflavin | 0.03764 | 0.22 |
| Thiamine HCl | 0.3373 | 2.17 |
| Thymidine | 0.37 | 0.7266 |
| Vitamin $B_{12}$ (cobalamine) | 0.68 | 4.07 |

In a still further aspect, the one or more tissue culture media may comprise DMEM/HAM's F-12 (1:1) and/or MCDB 153.

In another aspect of the preparation of the present invention, the one or more tissue culture media may be serum-free.

In another aspect, the preparation may further comprise a mixture comprising collagen, chitosan having a degree of acetylation of up to 50% and glycosylaminoglycan.

In another aspect, the preparation may further comprise one or more serum substitutes such as, e.g., one or more of chitosan, chrondroitin-6-sulfate and collagen. For example, the one or more serum substitutes may function as osmoregulators.

In yet another aspect, the preparation of the present invention may further comprise skin function inducers of plant origin and/or it may comprise glutamine.

In a still further aspect, the ratios of ingredients of the one or more cell culture media of mineral and organic biofactors may be suitable for the retention, the cultivation and the care of skin cells in vitro, ex vivo and/or in vivo.

In another aspect, the preparation may be present as an aqueous or aqueous-alcoholic solution, a spray, a foam, a foam aerosol, an ointment, an aqueous gel, an emulsion of the O/W, W/O or W/O/W type, a microemulsion and/or a cosmetic stick preparation. For example, the preparation may be present as a O/W emulsion.

In yet another aspect, the preparation may be present in anhydrous form such as, e.g., as a sponge or a powder.

The present invention also provides a method of treating healthy, irritated or diseased skin. The method comprises applying to the skin the preparation of the present invention, including the various aspects thereof set forth above.

The present invention also provides a method of treating skin, scalp or hair. The method comprises applying topically to the skin, scalp or hair the preparation of the present invention, including the various aspects thereof set forth above.

In one aspect of the method, the preparation may be applied in the form of an aqueous surfactant preparation, an emulsion, an ointment, a cream, a gel, a powder, a mask, a matrix plaster, a gel plaster, a foam or an aerosol preparation. For example, the preparation may be applied in the form of an O/W emulsion.

In another aspect of the method, the preparation may be applied in the form of a polyurethane matrix bandage.

In yet another aspect of the method, the preparation may be used for wound management or wound healing. For example, the preparation may be used in the form of a wound covering based on polyurethane.

The present invention also provides a process for making the preparation of the present invention. The process comprises mixing the one or more tissue culture media with one or more other cosmetic constituents of the preparation immediately prior to use.

The present invention also provides methods wherein the preparation of the present invention is used for one or more of:

a. the cultivation, the retention and/or the care in vitro, ex vivo and/or in vivo of fibroblast cells, keratinocyte cells, cocultures of keratinocytes and fibroblasts, cocultures of fibroblasts/keratinocytes and other skin-relevant cells, such as immune cells, melanocytes,
b. the generation of three-dimensional skin models,
c. the generation of immunocompetent three-dimensional skin models,
d. the retention and/or care of normal human skin in vitro, ex vivo and/or in vivo, in particular for the new cultivation of remaining skin cells, in particular for the treatment of burn injuries,
e. the retention and/or care of diseased human skin in vitro, ex vivo and/or in vivo, in particular for the regeneration of the skin, if appropriate following excision of the diseased areas of skin,
f. the retention and/or care of damaged human skin in vitro, ex vivo and/or in vivo, in particular for the regeneration of the skin from cells which remain in the case of ulcus cruris, contusions and burns.

It was surprising and unforeseeable for the person of skill in the art that a cosmetic and/or dermatological preparation comprising one or more tissue, in particular skin, cell culture media achieves the stated objects. It has been possible to show in numerous experiments that skin cell culture media which are suitable for cultivating organotypical skin cultures and for cultivating fibroblasts and keratinocytes are to be regarded as being advantageous for use in the cosmetic and/or dermatological preparations. In particular, the preparations in which the media is chosen from Ham's F10, Ham's F12 or MCDB, alone or as mixtures thereof, in particular DMEM/HAM's F-12 (1:1) and/or MCDB 153, are particularly advantageous.

In particular, serum-free preparations avoid the disadvantages stated in the prior art.

Experiments have shown that cell culture media are in principle suitable for tissues of all types, for the cultivation thereof, for aiding multiplication or exerting advantageous effects on the tissue.

The term tissue culture medium is understood by the person skilled in the art as meaning all liquid, semisolid or solid media or mixtures of mineral components, vitamins, enzymes, proteins, proteids or trace elements in which or on which the tissue, in particular skin cells, can multiply and/or be cultivated. The tissue culture media according to the invention are thus particularly suitable for cultivating skin cells of all types, but also for cultivating cells of non-dermal origin in the skin, such as melanocytes, Langerhans cells, Merkel cells etc. According to the invention, tissue is preferably regarded as being skin cell tissue. The skin cell culture media according to the invention accordingly include those media which are suitable, in terms of the composition of their individual constituents, for cultivating the following tissues:

1. Fibroblast cells, keratinocyte cells, cocultures of keratinocytes and fibroblasts, cocultures of fibroblasts/keratinocytes and further skin-relevant cells, such as immune cells, melanocytes etc.
2. Culture media for generating three-dimensional skin models
3. Culture media for generating immunocompetent three-dimensional skin models
4. Normal human skin in vitro, ex vivo and in vivo for the purpose of newly cultivating remaining skin cells, in particular for the treatment of burn injuries
5. Diseased human skin in vitro, ex vivo and in vivo, for the purpose of healthy regeneration of the skin, optionally following excision of the diseased areas of skin
6. Injured human skin in vitro, ex vivo and in vivo, for the purpose of regenerating the skin from remaining cells in the case of ulcus cruris, contusions and burns.

The use of skin-relevant culture media brings about autologous, healthy and individual regeneration of deficient skin functions in vivo. For example, the regeneration of the skin, skin tautness or else simply only the contribution to skin care can be significantly improved.

In principle, all tissue, in particular skin, cell culture media are suitable for use in cosmetic preparations. Of particular suitability and thus in accordance with the invention are, however, those skin cell culture media which are used in the literature for cultivating skin cells or skin-relevant cells, for treating skin irritations and burns. In particular, media for cultivating remaining cells after extensive burns show an extremely advantageous effect, namely a rapid, pain-free restoration of the starting state, of healthy skin, following application of the topical preparations.

Advantageous skin cell culture media according to the invention are also media which permit the retention and neogenesis of fibroblasts or keratinocytes alone or in mixed cultures. The ratios of the ingredients of the cell culture media of mineral or organic biofactors are chosen so that they are suitable for the retention, the cultivation and the care of skin cells in vitro, ex vivo and in vivo.

In particular, so-called serum-free media have proven advantageous if the cell fraction of the keratinocytes is to be influenced in a positive way in the sense of an optimized homeostasis.

Surprisingly, it has been possible to show that the cosmetic or dermatological preparations according to the invention which comprise skin cell culture media for cultivating skin cells are able, in or on the human skin itself, to activate those mechanisms which use the skin for homeostasis and autopoiesis. In this connection, it is possible for mixtures of fibroblast- and keratinocyte-relevant growth media to be used directly or in suitable vesicle technologies and be used for medical/pharmaceutical purposes and cosmetic purposes. Suitable vesicle systems are here preferably membrane systems, such as, for example, liposomes or cyclodextrin preparations, and microemulsions or nanoemulsions based on fluid or solid lipids. Advantages of these vesicular applications are the bringing of media to or through the skin barrier at their epidermal or dermal site of action.

This combination of skin cell culture media and vesicle technology, in particular cosmetic emulsion preparations, ensures an efficient treatment and care of the skin really for the first time. Through this synergistic combination of the provision of specific, in particular serum-free, skin cell culture media, incorporation in suitable topical preparations and application of these preparations to the skin, optimum conditions are created which allow the skin to regenerate itself and to be maintained in a healthy flow equilibrium, homeostasis, and also to stimulate autopoiesis.

According to the Maturana/Varela definition, autopoiesis means for living systems on the one hand strict autonomy, on the other hand this concept emphasizes the intensity and the degree of the interconnection between living systems and their environment. Autopoietic systems are structurally determined, i.e. they are structurally coupled to the medium and other living systems in interactions. For the skin, this autopoiesis means the permanent, healthy renewal from itself if the environmental conditions and nutrient supplies are adequate. These very conditions and supplies are provided by the preparations according to the invention.

According to the invention, particular preference is given to tissue culture media which comprise the following constituents in the concentration ranges given:

| Constituents of the medium | mg/liter Range Minimum | Maximum |
|---|---|---|
| Biotin | 0.0036 | 0.0146 |
| CaCl$_2$•2 H$_2$O | 4.41 | 116.61 |
| Calcium pantothenate | 0.25 | 2.24 |
| Choline chloride | 9 | 13.96 |
| CuSO$_4$•5 H$_2$O | 0.0002496 | 0.00125 |
| D-Glucose | 1081 | 3151 |
| FeSO$_4$•7 H$_2$O | 0.417 | 1.39 |
| Folic acid | 0.79 | 2.65 |
| Glycine | 7.51 | 18.75 |
| Inositol | 12.6 | 18.02 |
| KCl | 111.83 | 311.8 |
| L-Alanine | 4.5 | 8.91 |
| L-Arginine•HCl | 147.5 | 210.7 |
| L-Asparagine | 7.5 | 15.01 |
| L-Aspartic acid | 3.99 | 6.65 |
| L-Cysteine•HCl | 15.75 | 42.04 |
| L-Glutamine | 365.3 | 877.2 |
| L-Glutamic acid | 7.35 | 14.71 |
| L-Histidine•HCl•H$_2$O | 16.77 | 31.5 |
| Lipoic acid | 0.11 | 0.2063 |
| L-Isoleucine | 1.968 | 54.5 |
| L-Leucine | 59 | 65.6 |
| L-Lysine•HCl | 18.27 | 91.25 |
| L-Methionine | 4.475 | 17.24 |
| L-Phenylalanine | 4.956 | 35.5 |
| L-Proline | 17.25 | 34.53 |
| L-Serine | 26.25 | 63.06 |
| L-Threonine | 11.91 | 53.5 |
| L-Tyrosine | 2.718 | 38.7 |
| L-Valine | 35.13 | 52.85 |
| MgCl$_2$•6 H$_2$O | 61 | 122 |
| Na$_2$HPO$_4$•7 H$_2$O | 71 | 536.2 |
| NaCl | 6999.5 | 7599 |
| NaHCO$_3$ | 1176 | 2438 |
| Sodium pyruvate | 47 | 63 |
| Nicotinamide | 0.03663 | 2.02 |
| Pyridoxine HCl | 0.031 | 0.06171 |
| Riboflavin | 0.03764 | 0.22 |
| Thiamine HCl | 0.3373 | 2.17 |
| Thymidine | 0.37 | 0.7266 |
| Vitamin B$_{12}$ (cobalamine) | 0.68 | 4.07 |

A cosmetic preparation comprising a tissue culture medium comprising the constituents given in the table satisfies the object posed and is exceptionally suitable for the treatment of skin disorders and for skin care, hair care and scalp care.

The skin cell culture media DMEM/HAM's F-12 (1:1) and MCDB 153 are also particularly suitable here for the use according to the invention in cosmetic preparations.

Individual adaptations of these preparations are, however, advantageous. In this connection, these adaptations can consist in changing the serum substitute compositions or by varying the ratios of the concentrations of the media constituents. In addition, all of the modifications are possible which are prepared disregarding choline chloride, corresponding selenium salts, etc.

According to the literature information from Barnes D. and Sato G.; Anal. Biochem 102, 255 [1980], DMEM/HAM's F-12 (1:1) is a 1:1 mixture, the nutrient content of the Ham's F-12 medium being increased by adding Dulbecco's MEM (DMEM=Dulbesccos Modified Eagles medium). This medium is the basis for cultivating cell lines for human proteins, such as, for example, erythropoietin.

DMEM/HAM's F-12 (1:1) has the following composition (data in mg/l):

| | | | |
|---|---|---|---|
| NaCl | 6999.5 | L-Leucine | 59 |
| KCl | 311.8 | L-Lysine HCl | 91.25 |
| Na$_2$HPO$_4$ | 71 | L-Methionine | 17.24 |
| Na$_2$HPO$_4$—H$_2$O | 62.5 | L-Phenylalanine | 35.5 |
| MgSO$_4$—7H$_2$O | 100 | L-Proline | 17.25 |
| MgCl$_2$—6H$_2$O | 61 | L-Serine | 26.25 |
| CaCl$_2$ | 116.61 | L-Threonine | 53.5 |
| Fe(NO$_3$)$_3$—9H$_2$O | 0.05 | L-Tryptophan | 9 |
| FeSO$_4$—7H$_2$O | 0.417 | L-Tyrosine | 38.7 |
| CuSO$_4$—5H$_2$O | 0.00125 | L-Valine | 52.85 |
| ZnSO$_4$—7H$_2$O | 0.432 | Choline chloride | 9 |
| D-Glucose | 3151 | α-Biotin | 0.00365 |
| NaHCO$_3$ | 2438 | Folic acid | 2.65 |
| Na pyruvate | 55 | D-Ca pantothenate | 2.24 |
| Phenol red | 12.5 | Myo-inositol | 12.6 |
| L-Alanine | 4.5 | Nicotinamide | 2.02 |
| L-Arginine HCl | 147.5 | Pyridoxcal HCl | 2 |
| L-Asparagine-H$_2$O | 7.5 | Pyridoxine HCl | 0.031 |
| L-Aspartic acid | 6.65 | Riboflavin | 0.22 |
| L-Cysteine HCl | 15.75 | Thiamine HCl | 2.17 |
| L-Cystine | 24 | Vitamin B$_{12}$ | 0.68 |
| L-Glutamine | 365.3 | Hypoxanthin | 2.05 |
| L-Glutamic acid | 7.35 | Thymidine | 0.37 |
| Glycine | 18.75 | Lipoic acid | 0.11 |
| L-Histidine HCl—H$_2$O | 31.5 | Linoleic acid | 0.042 |
| L-Isoleucine | 54.5 | Putrescine 2HCl | 0.081 |

According to the literature reference Barnes D. and Sato G.; Anal. Biochem 102, 255 [1980], MCDB 153 is used for cultivating human keratinocytes. Also as minimal medium PBS, phosphate-buffered saline, with pH values from 3.5 to 8.

MCDB 153 has the following composition (mg/l):

| | | | |
|---|---|---|---|
| NaCl | 7599 | Choline chloride | 13.96 |
| KCl | 111.83 | Putrescine | 0.1611 |
| Sodium acetate-3H$_2$O | 500 | Vitamin 1312 | 4.07 |
| Na$_2$HPO$_4$—7H$_2$O | 536.2 | Biotin | 0.0146 |
| MgCl$_2$—6H$_2$O | 122 | Calcium pantothenate | 0.258 |
| CaCl$_2$—2H$_2$O | 4.411 | Nicotinamide | 0.03663 |
| Glucose | 1081 | Pyridoxine HCl | 0.06171 |
| Sodium pyruvate | 55 | Thiamine HCl | 0.3373 |
| NaHCO$_3$ | 1176 | Adenine | 24.32 |
| Phenol red | 1.317 | Myo-inositol | 18.02 |
| HEPES | 6600 | Lipoic acid | 0.2063 |
| Thymidine | 0.7266 | Folic acid | 0.79 |
| L-Alanine | 8.91 | Riboflavin | 0.03764 |
| L-Arginine HCl | 210.7 | CuSO$_4$—5H$_2$O | 0.0002496 |
| L-Asparagine | 15.01 | FeSO$_4$—7H$_2$O | 1.39 |
| L-Aspartic acid | 3.99 | MnSO$_4$—5H$_2$O | 0.000241 |
| L-Cysteine HCl—H$_2$O | 42.04 | (NH$_4$)$_6$Mo$_7$O$_{24}$—4H$_2$O | 0.001236 |
| L-Glutamine | 877.2 | NiCl$_2$—6H$_2$O | 0.0001188 |

-continued

| | | | |
|---|---|---|---|
| L-Glutamic acid | 14.71 | $H_2SeO_3$ | 0.003869 |
| Glycine | 7.51 | $Na_2SiO_3$—$9H_2O$ | 0.1421 |
| L-Histidine HCl—$H_2O$ | 16.77 | $SnCl_2$—$2H_2O$ | 0.0001128 |
| L-Isoleucine | 1.968 | $NH_4VO_3$ | 0.000585 |
| L-Leucine | 65.6 | $ZnSO_4$—$7H_2O$ | 0.144 |
| L-Lysine HCl | 18.27 | | |
| L-Methionine | 4.476 | | |
| L-Phenylalanine | 4.956 | | |
| L-Proline | 34.53 | | |
| L-Serine | 63.06 | | |
| L-Threonine | 11.91 | | |
| L-Tryptophan | 3.06 | | |
| L-Tyrosine | 2.718 | | |
| L-Valine | 35.13 | | |

The advantage of the DMEM/HAM's F-12 (1:1) and MCDB 153 media is that they permit, in cosmetic or dermatological preparations which are particularly selected and suitable for the cultivation of monolayer, two-dimensional and organotypical skin models, and the in vitro and ex vivo stimulation or retention of skin-specific biofunctions.

The tissue, in particular skin, cell culture media can easily be used as a constituent of the water phase in the cosmetic or dermatological preparations, it also being possible for them to completely replace the water phase of the preparation.

The fraction of the tissue culture media is therefore 0.1 up to 100% by weight, preferably 1 to 50% by weight, very particularly preferably 40% by weight, based on the total mass of the cosmetic preparation.

Thus, according to the invention, an aqueous preparation consisting of 100% by weight of skin cell culture medium, e.g. MCDB 153 as stated above, is to be used as cosmetic preparation.

Here, these media can be used on their own or in mixtures with relevant serum substitute factors, such as, for example, "serum substitute A" or "serum substitute B" from Seromed. The sera substitutes can be used by osmotic regulators from the groups of proteoglycans, glycoproteins, collagens, chitin derivatives (chitosan) or mixtures thereof, such as, for example, chitosan/chondroitin-6-sulfate/collagen or vegetable skin function inducers which are able to optimize the stimulation of essential factors in cell cultures. Suitable serum substitutes are also trace elements, such as, for example, the serum substitute A from Seromed and/or the addition of extracellular matrix substances, such as, for example, collagen, chondroitin-6-sulfate and chitosan.

The preparations comprising these media and, optionally, mixtures of serum substitutes (SES) such as, for example, the "chitosan/chondroitin-6-sulfate/collagen" used for burns (Damour et al., 1986) exhibit a particularly good effect on diseased, irritated or slightly damaged skin.

A particularly advantageous combination lies in the linkage of cell-nourishing culture media, preferably media for the culturing of skin or corneal cultures of all types, with a cellular matrix comprising collagen, chitosan with a degree of acetylation up to 50% and glycosylaminoglycan. The glycosylaminoglycan is chosen from chondroitin-4-sulfate and/or chondroitin-6-sulfate. Preference is therefore given in particular to a preparation comprising collagen, acetylated chitosan with a degree of acetylation of up to 50%, preferably up to 40%, and chondroitin sulfates. The collagen is preferably obtained from maritime collagens chosen from the group of type 3, type 1, type 4 and/or type 5 or mixtures thereof. This combination, on its own, in a mixture with cosmetic preparations or incorporated into polyurethane matrices, has proven extremely effective with regard to skin regeneration, skin care and wound healing. The invention enables the regeneration of skin or partial skin from individual cells (dermis and epidermis), and the transfer of this gel matrix pre-cultured in vitro to damaged tissue for complete skin renewal and/or the prevention or reduction of scar tissue during wound healing. The present invention also offers the ideal environment (matrix) for the renewal of the skin on topical application.

The preparation of the matrix is described in EP 296078. The disclosure content of EP 296078 is hereby incorporated into the present application in its entirety.

It is novel and unforeseeable for the person skilled in the art and thus in accordance with the invention that the matrix described in EP 296078 can also be obtained in its entirety by maritime and/or synthetic raw material sources and leads to the same results as described in EP 296078.

It is additionally possible to add solutions of the following compositions A or B advantageously as serum substitutes to the media, it being possible for the concentrations of the solutions to vary from 0.1 to 10,000 μg depending on the application.

| Solution A | | Solution B | |
|---|---|---|---|
| Components (1000x) | μM | Components (1000x) | μM |
| $FeSO_4$—$7H_2O$ | 3000 | Human insulin in 0.01 M HCl | 86 |
| $ZnSO_4$—$7H_2O$ | 3000 | | |
| $CoCl_2$—$6H_2O$ | 1000 | | |
| $CuSO_4$—$5H_2O$ | 10 | | |
| $Na_2SeO_3$ | 10 | | |
| $AlCl_3$—$6H_2O$ | 5 | | |
| $CrK(SO_4)_2$—$12H_2O$ | 1.4 | | |
| $NiCl_3$—$6H_2O$ | 1 | | |
| $MnCl_2$—$4H_2O$ | 1 | | |
| EDTA•$Na_2$—$2H_2O$ | 30000 | | |
| Polysorbate 80 VG | 3820 | | |

The serum substitutes are preferably used as osmoregulators.

According to information in the literature, the liquid media are usually prepared using high-purity, pyrogen-free water, corresponding to the WFI quality (water for injection) of Pharmacopeia Europe. The liquid media are sterilized by filtration and bottled, the systems and methods of manufacture being such that entry of endotoxins and microbes is substantially precluded. Besides high-purity, pyrogen-free water, however, it is also possible to use pure spring water.

The media according to the invention have advantageous properties in relation to skin regeneration even if the media composition is changed, such as, for example, with or without choline chloride, with or without $H_2SeO_3$.

Optionally, the media may have glutamine and/or stabilized glutamine, stabilized glutamine N-acetyl-alanyl glutamine added thereto. These combinations also have advantages.

The tissue, in particular skin, cell culture media and, if appropriate, additives are mixed into cosmetic or dermatological preparations in an amount of up 99.9% by weight, based on the total mass of the preparation.

Advantageously, the anhydrous application form, for example in the form of "sponges" or powders and thus also the 100% use of the skin cell culture media may also be possible for the skin treatment.

Depending on the field of use and the tissue to be treated, it is possible for the person skilled in the art, by modifying the media constituents, to arrive at an enhancement and optimization of the culture conditions. The culture conditions can thus be adapted individually to the specific purpose by employing the constituents and their fractions in modified form compared with the standard media.

Cosmetic or dermatological preparations are understood to mean topical preparations which are suitable for applying said media to the skin in a fine distribution and preferably in a form which can be absorbed by the skin. Of suitability here are, for example, aqueous and aqueous-alcoholic solutions, sprays, foams, foam aerosols, ointments, aqueous gels, emulsions of the O/W, W/O or W/O/W type, microemulsions or cosmetic stick preparations. Particularly preferred carriers are an aqueous gel, an O/W emulsion or a microemulsion. For the purposes of the invention, the preparation can also be used in body-cleansing compositions, such as, for example, soaps, shower baths, shampoos and the like.

The cosmetic formulations are in particular O/W emulsions.

All of the lipids known in cosmetics can be used as oil or lipid phase.

For the purposes of the present disclosure, the expression "lipids" is used as the generic term for fats, oils, waxes and the like, as is entirely familiar to the person skilled in the art. The terms "oil phase" and "lipid phase" are also used synonymously.

Suitable polar oils are, for example, those from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil and the like.

Particularly advantageous polar lipids for the purposes of the present invention are all native lipids, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil, corn germ oil, avocado oil and the like, and those listed below.

| Manufacturer | Trade name | INCI name | Polarity [mN/m] |
|---|---|---|---|
| Condea Chemie | Isofol 14 T | Butyl Decanol (+) Hexyl Octanol (+) Hexyl Decanol (+) Butyl Octanol | 19.8 |

-continued

| Manufacturer | Trade name | INCI name | Polarity [mN/m] |
|---|---|---|---|
| Lipochemicals INC./ ISA (Induchem) | Lipovol MOS-130 | Tridecyl Stearate (+) Tridecyl Trimellitate (+) Dipentaerythrityl Hexacaprylate/Hexacaprate | 19.4 |
| | Castor oil | | 19.2 |
| CONDEA Chemie | Isofol Ester 0604 | | 19.1 |
| Huels CONDEA Chemie | Miglyol 840 | Propylene Glycol Dicaprylate/Dicaprate | 18.7 |
| CONDEA Chemie | Isofol 12 | Butyl Octanol | 17.4 |
| Goldschmidt | Tegosoft SH | Stearyl Heptanoate | 17.8 |
| | Avocado oil | | 14.5 |
| Henkel Cognis | Cetiol B | Dibutyl Adipate | 14.3 |
| ALZO (ROVI) | Dermol 488 | PEG 2 Diethylene hexanoate | 10.1 |
| Condea Augusta S.P.A. | Cosmacol ELI | C12-13 Alkyl Lactate | 8.8 |
| ALZO (ROVI) | Dermol 489 | Diethylene Glycol Dioctanoate/Diisononanoate | 8.6 |
| Condea Augusta S.P.A. | Cosmacol ETI | Di-C12/13 Alkyl Tartrate | 7.1 |
| Henkel Cognis | Emerest 2384 | Propylene Glycol Monoisostearate | 6.2 |
| Henkel Cognis | Myritol 331 | Cocoglycerides | 5.1 |
| Unichema | Prisorine 2041 GTIS | Triisostearin | 2.4 |

In addition, the oil phase can advantageously be chosen from the group of dialkyl ethers, the group of saturated or unsaturated, branched or unbranched alcohols. It is particularly advantageous if the oil phase has a content of $C_{12-15}$-alkyl benzoate or consists entirely thereof.

In addition, the oil phase can be chosen advantageously from the group of Guerbet alcohols. Guerbet alcohols are named after Marcel Guerbet, who described their preparation for the first time. They are formed according to the reaction equation

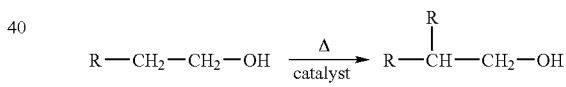

by oxidation of an alcohol to give an aldehyde, by aldol condensation of the aldehyde, elimination of water from the aldol and hydrogenation of the allyl aldehyde. Guerbet alcohols are liquid even at low temperatures and cause virtually no skin irritations. They can be used advantageously as fatting, superfatting and also refatting constituents in skin care and hair care compositions.

The use of Guerbet alcohols in cosmetics is known per se. Such species are in most cases characterized by the structure

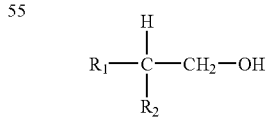

Here, $R_1$ and $R_2$ are usually unbranched alkyl radicals.

According to the invention, the Guerbet alcohol or alcohols are chosen from the group in which $R_1$=propyl, butyl, pentyl, hexyl, heptyl or octyl and $R_2$=hexyl, heptyl, octyl, nonyl, decyl, undecyl, dodecyl, tridecyl or tetradecyl.

Guerbet alcohols preferred according to the invention are 2-butyloctanol which has the chemical structure

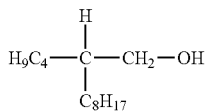

and is available, for example, under the trade name Isofol® 12 from Condea Chemie GmbH, and 2-hexyldecanol which has the chemical structure

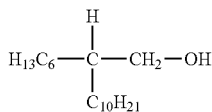

and is available, for example, under the trade name Isofol® 16 from Condea Chemie GmbH. Mixtures of Guerbet alcohols according to the invention may also be used advantageously according to the invention. Mixtures of 2-butyloctanol and 2-hexyldecanol are available, for example, under the trade name Isofol® 14 from Condea Chemie GmbH.

The total amount of Guerbet alcohols in the finished cosmetic or dermatological preparations is advantageously chosen from the range of up to 25.0% by weight, preferably 0.5-15.0% by weight, based on the total weight of the preparations.

Any desired mixtures of such oil and wax components are also used advantageously for the purposes of the present invention. It may in some cases also be advantageous to use waxes, for example cetyl palmitate, as the sole lipid component of the oil phase.

Particularly advantageous medium-polar lipids for the purposes of the present invention are the substances listed below:

| Manufacturer | Trade name | INCI name | Polarity [mN/m] |
|---|---|---|---|
| Stearinerie Dubois Fils | DUB VCI 10 | Isodecyl Neopentanoate | 29.9 |
| ALZO (ROVI) | Dermol IHD | Isohexyl Decanoate | 29.7 |
| ALZO (ROVI) | Dermol 108 | Isodecyl Octanoate | 29.6 |
| | Dihexyl Ether | Dihexyl Ether | 29.2 |
| ALZO (ROVI) | Dermol 109 | Isodecyl 3,5,5 Trimethyl Hexanoate | 29.1 |
| Henkel Cognis | Cetiol SN | Cetearyl Isononanoate | 28.6 |
| Unichema | Isopropyl palmitate | Isopropyl Palmitate | 28.8 |
| Dow Corning | DC Fluid 345 | Cyclomethicone | 28.5 |
| Dow Corning | Dow Corning Fluid 244 | Cyclopolydimethyl-siloxane | 28.5 |
| Nikko Chemicals Superior Jojoba Oil Gold | Jojoba oil Gold | | 26.2 |
| Wacker | Wacker AK 100 | Dimethicone | 26.9 |
| ALZO (ROVI) | Dermol 98 | 2-Ethylhexanoic acid 3,5,5 Trimethyl ester | 26.2 |
| Dow Corning | Dow Corning Fluid 246 | open | 25.3 |
| Henkel Cognis | Eutanol G | Octyldodecanol | 24.8 |
| Condea Chemie | Isofol 16 | Hexyl Decanol | 24.3 |
| ALZO (ROVI) | Dermol 139 | Isotridecyl 3,5,5 Trimethylhexanonanoate | 24.5 |
| Henkel Cognis | Cetiol PGL | Hexyldecanol (+) Hexyl Decyl Laurate | 24.3 |
| | Cegesoft C24 | Octyl Palmitate | 23.1 |
| Gattefossé | M.O.D. Macadamia Nut Oil | Octyldodecyl Myristate | 22.1 / 22.1 |
| Bayer AG, Dow Corning | Silicone oil VP 1120 | Phenyl Trimethicone | 22.7 |
| CONDEA Chemie | Isocarb 12 | Butyl Octanoic acid | 22.1 |
| Henkel Cognis | Isopropyl stearate | Isopropyl Stearate | 21.9 |
| WITCO, Goldschmidt | Finsolv TN | C12-15 Alkyl Benzoate | 21.8 |
| Dr. Straetmans | Dermofeel BGC | Butylene Glycol Caprylate/Caprate | 21.5 |
| Unichemia Huels | Miglyol 812 | Caprylic/Capric Triglyceride | 21.3 |
| Trivent (via S. Black) | Trivent OCG | Tricaprylin | 20.2 |
| ALZO (ROVI) | Dermol 866 | PEG Diethylhexanoate/ Diisononanoate/ Ethylhexyl Isononanoate | 20.1 |

Nonpolar oils are, for example, those which are chosen from the group of branched and unbranched hydrocarbons and hydrocarbon waxes, in particular vaseline (petrolatum), paraffin oil, squalane and squalene, polyolefins and hydrogenated polyisobutenes. Among the polyolefins, polydecenes are the preferred substances.

Particularly advantageous nonpolar lipids for the purposes of the present invention are the substances listed below:

| Manufacturer | Trade name | INCI name | Polarity [mN/m] |
|---|---|---|---|
| Total SA | Ecolane 130 | Cycloparaffin | 49.1 |
| Neste PAO N.V. (supplier Hansen & Rosenthal) | Nexbase 2006 FG | Polydecene | 46.7 |
| Chemische Fabrik Lehrte | Polysynlane | Hydrogenated Polyisobutene | 44.7 |
| Wacker | Wacker Silicone oil AK 50 | Polydimethylsiloxane | 46.5 |
| EC Erdölchemie (supplier Bayer AG) | Solvent ICH | Isohexadecane | 43.8 |
| DEA Mineral oil (supplier Hansen & Rosenthal) Tudapetrol | Pionier 2076 | Mineral Oil | 43.7 |
| DEA Mineral oil (supplier Hansen & Rosenthal) Tudapetrol | Pionier 6301 | Mineral Oil | 43.7 |
| Wacker | Wacker silicone oil AK 35 | Polydimethylsiloxane | 42.4 |
| EC Erdölchemie GmbH | Isoeicosane | Isoeicosane | 41.9 |
| Wacker | Wacker Silicone oil AK 20 | Polydimethylsiloxane | 40.9 |
| Condea Chemie | Isofol 1212 Carbonate | | 40.3 |
| Gattefossé | Softcutol O | Ethoxydiglycol Oleate | 40.5 |
| Creaderm | Lipodermanol OL | Decyl Olivate | 40.3 |
| Henkel | Cetiol S | Dioctylcyclohexane | 39.0 |
| DEA Mineral oil (supplier Hansen & Rosenthal) Tudapetrol | Pionier 2071 | Mineral Oil | 38.3 |
| WITCO BV | Hydrobrite 1000 PO | Paraffinum Liquidum | 37.6 |
| Goldschmidt | Tegosoft HP | Isocetyl Palmitate | 36.2 |
| Condea Chemie | Isofol Ester 1693 | | 33.5 |
| Condea Chemie | Isofol Ester 1260 | | 33.0 |

| Manufacturer | Trade name | INCI name | Polarity [mN/m] |
|---|---|---|---|
| Dow Corning | Dow Corning Fluid 245 | Cyclopentasiloxane | 32.3 |
| Unichema | Prisorine 2036 | Octyl Isostearate | 31.6 |
| Henkel Cognis | Cetiol CC | Dicarpylyl Carbonate | 31.7 |
| ALZO (ROVI) | Dermol 99 | Trimethylhexyl Isononanoate | 31.1 |
| ALZO (ROVI) | Dermol 89 | 2-Ethylhexyl Isononanoate | 31.0 |
| Henkel Cognis | Cetiol OE | Dicaprylyl Ether | 30.9 |
| | Dihexyl carbonate | Dihexyl Carbonate | 30.9 |
| Albemarle S.A. | Silkflo 366 NF | Polydecene | 30.1 |
| Unichema | Estol 1540 EHC | Octyl Cocoate | 30.0 |

However, it is also advantageous to use mixtures of lipids with higher and lower polarity and the like. For example, the oil phase can advantageously be chosen from the group of branched and unbranched hydrocarbons and hydrocarbon waxes, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids with a chain length of from 8 to 24, in particular 12-18, carbon atoms. The fatty acid triglycerides can, for example, be chosen advantageously from the group of synthetic, semisynthetic and natural oils, e.g. olive oil, sunflower oil, soya oil, peanut oil, rapeseed oil, almond oil, palm oil, coconut oil, palm kernel oil and the like, provided the conditions required in the main claim are met.

Fat and/or wax components to be used advantageously according to the invention can be chosen from the group of vegetable waxes, animal waxes, mineral waxes and petrochemical waxes. According to the invention, candelilla wax, carnauba wax, Japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresine, ozokerite (earth wax), paraffin waxes and microwaxes, for example, are favorable, provided the conditions required in the main claim are met.

Further advantageous fat and/or wax components are chemically modified waxes and synthetic waxes, such as, for example, those available under the trade names Syncrowax HRC (glyceryl tribehenate), and Syncrowax AW 1C($C_{18-36}$-fatty acid) from CRODA GmbH, and montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkyl hydroxystearoylstearate and/or glycol montanate. In addition, also advantageous are certain organosilicon compounds which have similar physical properties to said fat and/or wax components, such as, for example, stearoxytrimethylsilane, provided the conditions required in the main claim are met.

According to the invention, the fat and/or wax components can either be present individually or as a mixture. Any desired mixtures of such oil and wax components may also be used advantageously for the purposes of the present invention.

The oil phase is advantageously chosen from 2-ethylhexyl isostearate, octyldodecanol, isotridecyl isononanoate, butylene glycol dicaprylate/dicaprate, 2-ethylhexyl cocoate, $C_{12-15}$-alkyl benzoate, caprylic/capric triglyceride, dicaprylyl ether, provided the conditions required in the main claim are met.

Mixtures of octyldodecanol, caprylic/capric triglyceride, dicaprylyl ether, dicaprylyl carbonate, cocoglycerides, or mixtures of $C_{12-15}$-alkyl benzoate and 2-ethylhexyl isostearate, mixtures of $C_{12-15}$-alkyl benzoate and butylene glycol dicaprylate/dicaprate, and mixtures of $C_{12-15}$-alkyl benzoate, 2-ethylhexyl isostearate and isotridecyl isononanoate are particularly advantageous, provided the conditions required in the main claim are met.

Of the hydrocarbons, paraffin oil, cycloparaffin, squalane, squalene, hydrogenated polyisobutene and polydecene may be used advantageously for the purposes of the present invention.

It may likewise be advantageous to choose the oil phase of the preparations according to the invention partially or completely from the group of cyclic and/or linear silicones, which are also referred to as "silicone oils" for the purposes of the present disclosure. Such silicones or silicone oils may be in the form of monomers which are generally characterized by the following structural elements:

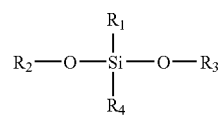

Silicone oils are high molecular weight synthetic polymeric compounds in which silicon atoms are joined via oxygen atoms in a chain-like and/or grid-like manner and the remaining valencies of the silicon are saturated by hydrocarbon radicals (in most cases methyl groups, less often ethyl, propyl, phenyl groups, inter alia).

Linear silicones with a plurality of siloxyl units which may advantageously be used according to the invention are generally characterized by the following structural elements:

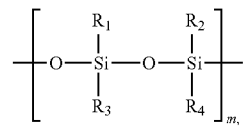

where the silicon atoms may be substituted by identical or different alkyl radicals and/or aryl radicals, which are shown here in general terms by the radicals $R_1$-$R_4$ (that is to say the number of different radicals is not necessarily limited to up to 4). m can assume values from 2 to 200,000.

Systematically, the linear silicone oils are referred to as polyorganosiloxanes; the methyl-substituted polyorganosiloxanes, which represent the most important compounds of this group in terms of amount are characterized by the following structural formula

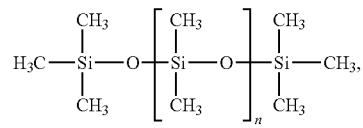

And are also referred to as polydimethylsiloxane or Dimethicone (INCI). Dimethicones have various chain lengths and various molecular weights. Dimethicones of various chain lengths and phenyltrimethicones are particularly advantageous linear silicone oils for the purposes of the present invention.

Particularly advantageous polyorganosiloxanes for the purposes of the present invention are also, for example, dimethylpolysiloxanes [poly(dimethylsiloxane)], which are available, for example, under the trade names ABIL 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to according to INCI as Cyclomethicone, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil Wax grades from Th. Goldschmidt.

Also particularly advantageous for the purposes of the present invention are the silicone oils listed below:

| Manufacturer | Trade Name | INCI name | Polarity [mN/m] |
| --- | --- | --- | --- |
| Wacker | Wacker silicone oil AK 100 | Polydimethylsiloxane | 26.9 |
| Wacker | Wacker silicone oil AK 50 | Polydimethylsiloxane | 46.5 |
| Wacker | Wacker silicone oil AK 35 | Polydimethylsiloxane | 42.4 |
| Wacker | Wacker silicone oil AK 20 | Polydimethylsiloxane | 40.9 |
| Dow Corning | Dow Corning Fluid 245 | Cyclopentasiloxane | 32.3 |
| Dow Corning | Dow Corning Fluid 345 | Cyclomethicone | 28.5 |

Cyclic silicones to be used advantageously according to the invention are generally characterized by the following structural elements:

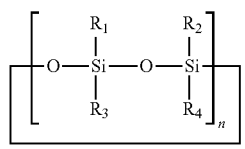

where the silicon atoms can be substituted by identical or different alkyl radicals and/or aryl radicals, which are represented here in general terms by the radicals $R_1$-$R_4$ (that is to say that the number of different radicals is not necessarily limited to up to 4). n can assume values of from 3/2 to 20. Fractional values for n take into account that odd numbers of siloxyl groups may be present in the ring.

Particularly advantageous cyclic silicone oils for the purposes of the present invention are cyclomethicones, in particular cyclomethicone D5 and/or cyclomethicone D6.

Advantageous silicone oils and silicone waxes for the purposes of the present invention are cyclic and/or linear silicone oils and silicone waxes.

It is particularly advantageous for the purposes of the present invention to choose the ratio of lipids to silicone oils to be about 1:1 (generally x:y).

Phenyltrimethicone is advantageously chosen as silicone oil. Other silicone oils, for example dimethicone, phenyldimethicone, cyclomethicone (octamethylcyclotetrasiloxane), for example hexamethylcyclotrisiloxane, polydimethylsiloxane, poly(methylphenylsiloxane), cetyldimethicone, behenoxydimethicone, may also be used advantageously for the purposes of the present invention.

Also advantageous are mixtures of cyclomethicone and isotridecyl isononanoate, and those of cyclomethicone and 2-ethylhexyl isostearate.

It is, however, also advantageous to choose silicone oils of similar constitution to the above-mentioned compounds whose organic side chains are derivatized, for example polyethoxylated and/or polypropoxylated. These include, for example, polysiloxane-polyalkyl-polyether copolymers, such as cetyl dimethicone copolyol, and cetyl dimethicone copolyol (and) polyglyceryl 4-isostearate (and) hexyl laurate.

Preparations according to the invention which are in the form of emulsions comprise one or more emulsifiers. These emulsifiers may be chosen advantageously from the group of nonionic, anionic, cationic or amphoteric emulsifiers.

The nonionic emulsifiers include
a) partial fatty acid esters and fatty acid esters of polyhydric alcohols and ethoxylated derivatives thereof (e.g. glyceryl monostearate, sorbitan stearate, glyceryl stearyl citrate, sucrose stearate)
b) ethoxylated fatty alcohols and fatty acids
c) ethoxylated fatty amines, fatty acid amides, fatty acid alkylamides
d) alkylphenol polyglycol ethers (e.g. Triton X).

The anionic emulsifiers include
a) soaps (e.g. sodium stearate)
b) fatty alcohol sulfates
c) mono-, di- and trialkyl phosphoric esters and ethoxylates thereof.

The cationic emulsifiers include
a) quaternary ammonium compounds with a long-chain aliphatic radical, e.g. distearyldimonium chloride.

The amphoteric emulsifiers include
a) alkylamininoalkanecarboxylic acids
b) betaines, sulfobetaines
c) imidazoline derivatives.

There are also naturally occurring emulsifiers, which include beeswax, wool wax, lecithin and sterols.

O/W emulsifiers can, for example, be chosen advantageously from polyethoxylated or polypropoxylated or polyethoxylated and polypropoxylated products, e.g.:
fatty alcohol ethoxylates
ethoxylated wool wax alcohols
polyethylene glycol ethers of the general formula R—O—(—CH$_2$—CH$_2$—O—)$_n$—R',
fatty acid ethoxylates of the general formula

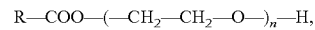

etherified fatty acid ethoxylates of the general formula

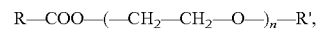

esterified fatty acid ethoxylates of the general formula

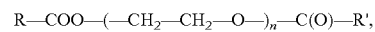

polyethylene glycol glycerol fatty acid esters
ethoxylated sorbitan esters
cholesterol ethoxylates
ethoxylated triglycerides
alkyl ether carboxylic acids of the general formula

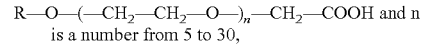

is a number from 5 to 30, polyoxyethylene sorbitol fatty acid esters,
alkyl ether sulfates of the general formula R—O—(—CH$_2$—CH$_2$—O—)$_n$—SO$_3$—H
fatty alcohol propoxylates of the general formula R—O—(—CH$_2$—CH(CH$_3$)—O—)$_n$—H, polypropylene glycol ethers of the general formula R—O—(—CH$_2$—CH(CH$_3$)—O—)$_n$—R', propoxylated wool wax alcohols,
etherified fatty acid propoxylates R—COO—(—CH$_2$—CH(CH$_3$)—O—)$_n$—R', esterified fatty acid propoxylates of the general formula R—COO—(—CH$_2$—CH(CH$_3$)—O—)$_n$—C(O)—R', fatty acid propoxylates of the general formula R—COO—(—CH$_2$—CH(CH$_3$)—O—)$_n$—H, polypropylene glycol glycerol fatty acid esters
propoxylated sorbitan esters
cholesterol propoxylates
propoxylated triglycerides
alkyl ether carboxylic acids of the general formula R—O—(—CH$_2$—CH(CH$_3$)—O—)$_n$—CH$_2$—COOH, alkyl ether sulfates and the acids on which these sulfates are based and of the general formula R—O—(—CH$_2$—CH(CH$_3$)—O—)$_n$—SO$_3$—H,
fatty alcohol ethoxylates/propoxylates of the general formula R—O—X$_n$—Y$_m$—H, polypropylene glycol ethers of the general formula R—O—X$_n$—Y$_m$—R', etherified fatty acid propoxylates of the general formula R—COO—X$_n$—Y$_m$—R', fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously chosen from substances with HLB values of 11-18, very particularly advantageously with HLB values of 14.5-15.5, if the O/W emulsifiers have saturated radicals R and R'. If the O/W emulsifiers have unsaturated radicals R and/or R', or if isoalkyl derivatives are present, then the preferred HLB value of such emulsifiers may also be lower or higher.

It is advantageous to choose the fatty alcohol ethoxylates from the group of ethoxylated stearyl alcohols, cetyl alcohols, cetylstearyl alcohols (cetearyl alcohols). Particular preference is given to:
polyethylene glycol(13) stearyl ether (steareth-13), polyethylene glycol(14) stearyl ether (steareth-14), polyethylene glycol(15) stearyl ether (steareth-15), polyethylene glycol (16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20),
polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20),
polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20),
polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol (17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20),
polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15),
polyethylene glycol(12) lauryl ether (laureth-12), polyethylene glycol(12) isolauryl ether (isolaureth-12),
polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), polyethylene glycol(20) cetylstearyl ether (ceteareth-20).

It is also advantageous to choose the fatty acid ethoxylates from the following group:
polyethylene glycol(20) stearate, polyethylene glycol(21) stearate, polyethylene glycol(22) stearate, polyethylene glycol(23) stearate, polyethylene glycol(24) stearate, polyethylene glycol(25) stearate,
polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol (18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate,
polyethylene glycol(12) oleate, polyethylene glycol(13) oleate, polyethylene glycol(14) oleate, polyethylene glycol(15) oleate, polyethylene glycol(16) oleate, polyethylene glycol (17) oleate, polyethylene glycol(18) oleate, polyethylene glycol(19) oleate, polyethylene glycol(20) oleate.

An ethoxylated alkyl ether carboxylic acid or salt thereof which can be used advantageously is sodium laureth-11 carboxylate.

Sodium laureth 1-4 sulfate can be used as alkyl ether sulfate.

An ethoxylated cholesterol derivative which can be used advantageously is polyethylene glycol(30) cholesterol ether. Polyethylene glycol(25) soyasterol has also proven useful.

Ethoxylated triglycerides which can be used advantageously are the polyethylene glycol(60) evening primrose glycerides.

It may also be advantageous to choose the polyethylene glycol glyceryl fatty acid esters from polyethylene glycol(20) glyceryl laurate, polyethylene glycol(21) glyceryl laurate, polyethylene glycol(22) glyceryl laurate, polyethylene glycol

(23) glyceryl laurate, polyethylene glycol(6) glyceryl caprate/caprinate, polyethylene glycol(20) glyceryl oleate, polyethylene glycol(20) glyceryl isostearate, polyethylene glycol(18) glyceryl oleate/cocoate.

It is likewise favorable to choose the sorbitan esters from polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

Advantageous W/O emulsifiers which may be used are: fatty alcohols having 8 to 30 carbon atoms, monoglycerol esters of saturated and/or unsaturated, branched and/or unbranched alkanecarboxylic acids with a chain length of from 8 to 24, in particular 12-18, carbon atoms, diglycerol esters of saturated and/or unsaturated, branched and/or unbranched alkanecarboxylic acids with a chain length of from 8 to 24, in particular 12-18, carbon atoms, monoglycerol ethers of saturated and/or unsaturated, branched and/or unbranched alcohols with a chain length of from 8 to 24, in particular 12-18, carbon atoms, diglycerol ethers of saturated and/or unsaturated, branched and/or unbranched alcohols with a chain length of from 8 to 24, in particular 12-18, carbon atoms, propylene glycol esters of saturated and/or unsaturated, branched and/or unbranched alkanecarboxylic acids with a chain length of from 8 to 24, in particular 12-18, carbon atoms, and sorbitan esters of saturated and/or unsaturated, branched and/or unbranched alkanecarboxylic acids with a chain length of from 8 to 24, in particular 12-18, carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprinate, glyceryl monocaprylate.

The specified emulsifier systems can be added to the preparations. Suitable emulsifier systems are advantageously steareth-2, steareth 21 and PEG-20-100 stearate.

Besides water and physiologically suitable solvents, care constituents, oils, waxes, fats, refatting substances, antioxidants, emulsifiers, substances suitable as sunscreen filters, enzymes, amino acids, proteins, polysaccharides and/or fragrances, inter alia, may be present. According to the invention, apart from the abovementioned substances, the preparations optionally comprise the additives customary in cosmetics, for example perfume, dyes, antimicrobial substances, refatting agents, complexing and sequestering agents, pearlizing agents, plant extracts, vitamins, active ingredients, preservatives, bactericides, pigments which have a coloring effect, thickeners, softening, moisturizing and/or humectant substances, or other customary constituents of a cosmetic or dermatological formulation, such as alcohols, polyols, polymers, foam stabilizers, electrolytes, organic solvents or silicone derivatives.

Suitable preparations are also those which can be used for professional wound dressing and/or wound healing, such as, for example, polyurethane preparations or wound coverings, chitosan/collagen/chondroitin 6-sulfate sponges or solutions.

The skin cell culture media can, for example, also be incorporated into polymer matrices, such as, in particular, polyurethane matrices, and be used as wound coverings. The incorporation can be carried out directly or advantageously with encapsulation. Suitable encapsulation materials are familiar to the person skilled in the art and known from the prior art.

The antioxidants added may advantageously be chosen from amino acids (e.g. glycine, lysine, arginine, cysteine, histidine, tyrosine, tryptophan) and derivatives thereof (as salt, ester, ether, sugar, nucleotide, nucleoside, peptide and lipid compound), imidazoles (e.g. urocanic acid) and derivatives thereof (as salt, ester, ether, sugar, nucleotide, nucleoside, peptide and/or lipid compound), peptides, such as D,L-carnosine, D-carnosine, L-carnosine, anserine and derivatives thereof (e.g. as salt, ester, ether, sugar, thiol, nucleotide, nucleoside, peptide and lipid compound), carotenoids, carotenes (e.g. α-carotene, β-carotene, ψ-lycopine, phytoene) and derivatives thereof (e.g. as salt, ester, ether, sugar, nucleotide, nucleoside, peptide and/or lipid compound), chlorogenic acid and derivatives thereof (as salt, ester, ether, sugar, thiol, nucleotide, nucleoside, peptide and/or lipid compound), aurothioglucose, propylthiouracil and other thiols (e.g. thioredoxin, lipoic acid, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (as salt, ester, ether, sugar, thiol, nucleotide, nucleoside, peptide and/or lipid compound), and sulfoximine compounds (e.g. homocysteine sulfoximine, buthionine sulfones, penta-, hexa-, heptathionine sulfoximine) in very low tolerated doses (e.g. pmol to µmol/kg). Also (metal) chelating agents (e.g. apoferritin, desferral, lactoferrin, α-hydroxy fatty acids, palmitic acid, phytic acid) and derivatives thereof (as salt, ester, ether, sugar, thiol, nucleotide, nucleoside, peptide and/or lipid compound), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (eg. γ-linolenic acid, linoleic acid, oleic acid), folic acid and derivatives thereof, furfurylidenesorbitol and derivatives thereof, ubiquinone, ubiquinol, plastoquinone and derivatives thereof (as salt, ester, ether, sugar, thiol, nucleotide, nucleoside, peptide and lipid compound), vitamin C and derivatives (e.g. ascorbyl palmitate, Mg ascorbyl phosphate, ascorbyl acetate), tocopherols and derivatives (e.g. vitamin E acetate), and phenolic compounds and plant extracts comprising these, such as, for example, flavonoids (e.g. glycosylrutin, ferulic acid, caffeic acid), furfurylideneglucitol, butylhydroxytoluene, butylhydroxyanisole, nordihydroguaiac acid, nordihydroguaiaretic acid, trihydroxybutyrophenone and derivatives thereof (as salt, ester, ether, sugar, nucleotide, nucleoside, peptide and lipid compound), uric acid and derivatives thereof, mannose and derivatives thereof (as salt, ester, ether, sugar, thiol, nucleotide, nucleoside, peptide and lipid compound), zinc and derivatives thereof (e.g. ZnO, $ZnSO_4$), selenium and derivatives thereof (e.g. selenomethionine, ebselen), stilbenes and derivatives (e.g. stilbene oxide, trans-stilbene oxide) and the derivatives suitable according to the invention (as salt, ester, ether, sugar, thiol, nucleotide, nucleoside, peptide and/or lipid compound) of these specified active ingredients.

An additional use of a buffer is not necessary since the pH fluctuations in the preparations according to the invention are negligibly small. pH adjustment of the finished preparation to a value corresponding to a suitable value for application to the human skin is advantageous.

The preparations according to the invention may be prepared, for example, as emulsion in accordance with known production processes. Here, an emulsion is firstly formed from the oil phase and the water phase and then the aqueous cell culture media phase is added.

The incorporation of the cell culture media into the cosmetic formulations should take place, on account of the thermolability of the medium, at at most 48° C., preferably at less than 35° C., ideally at 30° C.

The medium is added slowly and a temperature fluctuation of more than max. 4-5° C. should be avoided.

The medium is advantageously stored and also used at refrigerator temperatures, thus avoiding excessive cooling during the preparation, since this can, in some circumstances, lead to crystallizations and inhomogeneities.

The producibility is, in particular, however also possible at higher temperatures and the preparations according to the invention are particularly effective when used at temperatures around the body temperature range.

A disadvantage of cosmetic preparations from the prior art is their instability and the preservation problems. These can be ensured through the choice of suitable formulation technologies, such as, for example, twin-chamber systems, cartridge packagings or multiple emulsions. Cell culture media are just as suitable for stabilizing W/O/W technologies as physiological saline solutions.

Initial attempts, so-called preservative load tests of the preparations according to the invention exhibited no susceptibilities to build-up of germs. Tests with cosmetically customary use concentrations of preservatives were carried out.

TABLE 1 gives a list of the preservatives used.

| Preparation No. | Preservative | INCI | Use concentration in % |
|---|---|---|---|
| 1-1 | Unicide | Imidazolidinyl Urea | 0.3 |
|  | Uniphen | Phenoxyethanol (74%) Methylparaben (15%) Ethylparaben (4%) Butylparaben (4%) Isobutylparaben (2%) Propylparaben (1%) | 1.3 |
|  | Unistab S-69 | Farnesol | 0.5 |
|  | Unicide | Imidazolidinyl Urea | 0.3 |
| 1-2 | Uniphen | Phenoxyethanol (74%) Methylparaben (15%) Ethylparaben (4%) Butylparaben (4%) Isobutylparaben (2%) Propylparaben (1%) | 1.3 |
|  | Unistab S-69 | Farnesol | 0.5 |
| 2-1 | Nipagin M | Methylparaben | 0.3 |
|  | Uniphen | Phenoxyethanol (74%) Methylparaben (15%) Ethylparaben (4%) Butylparaben (4%) Isobutylparaben (2%) Propylparaben (1%) | 1.0 |
| 4-1 | Unicide | Imidazolidinyl Urea | 0.3 |
|  | Uniphen | Phenoxyethanol (74%) Methylparaben (15%) Ethylparaben (4%) Butylparaben (4%) Isobutylparaben (2%) Propylparaben (1%) | 1.0 |

The tested formulations 1-1, 1-2, 2-1, 4-1 are O/W emulsions and a cleansing lotion (2-1).

Preparation 1-1 and 2-1 comprises the keratinocyte medium MCDB 153, preparation 1-2 and 4-1 DMEM/HAM's F-12. The emulsifier system is identical for samples 1-1 and 1-2.

All of the load tests showed positive results, i.e. no instabilities or build-ups of germs of any kind.

Despite the excellent stability of the preparations according to the invention, it is nevertheless advisable to choose the packaging of the cosmetic so that it offers optimum protection of the cosmetic against the build-up of germs.

The packaging should be chosen in accordance with microbiological guidelines so as not to permit possible recontamination by the customer.

In the case of problematic formulations where the cell medium cannot be incorporated immediately during the production of the preparation, there is the option of mixing the cell culture medium and the cosmetic product just prior to use. This is ensured according to the invention by special packaging elements, such as, for example, twin cartridges with mixing head, as are known, for example, from 2-component adhesives. The packaging of the cell culture medium could also be designed to be topped up so that only fresh product is used. In this connection, as mentioned, the use of pulverulent or solid skin cell culture media is also possible.

DETAILED DESCRIPTION OF THE INVENTION

Advantageous working examples of the present invention are given below. Unless stated otherwise, the quantitative data refers to percent by weight, based on the total weight of the preparation.

Example 1

O/W Emulsion

| | |
|---|---|
| WATER (AQUA) | 69% |
| of which KERATINOCYTE MEDIA MCDB 153 | 40% |
| GLYCEROL | 4.3% |
| HYDROGENATED COCOGLYCERIDES | 3.0% |
| SQUALANE | 2.5% |
| GLYCERYL STEARATE CITRATE | 2.5% |
| CAPRYLIC/CAPRIC TRIGLYCERIDE | 2.5% |
| ETHYLHEXYL COCOATE | 2.3% |
| MYRISTYL ALCOHOL | 2.2% |
| BUTYROSPERMUM PARKII (SHEA BUTTER) | 2.0% |
| BUTYLENE GLYCOL | 2.0% |
| CETYL ALCOHOL | 1.8% |
| TOCOPHERYL ACETATE | 2.0% |
| PHENOXYETHANOL | 0.74% |
| SODIUM CHLORIDE | 0.33% |
| IMIDAZOLIDINYL UREA | 0.3% |
| CARBOMER | 0.26% |
| XANTHAN GUM | 0.2% |
| METHYLPARABEN | 0.15% |
| EDTA | 0.1% |
| SODIUM HYDROXIDE | 0.05% |
| BHT | 0.05% |
| ETHYLPARABEN | 0.04% |
| BUTYLPARABEN | 0.04% |
| ISOPROPYLPARABEN | 0.02% |
| PROPYLPARABEN | 0.01% |

Example 2

W/O/W Emulsion

| | |
|---|---|
| PEG-100 stearate | 2.00% |
| Glyceryl stearate | 4.00% |
| Squalane | 1.50% |
| Squalene | 1.50% |
| Isopropyl palmitate | 5.40% |
| Magnesium sulfate | 0.60% |
| Preservative | 0.50% |
| Water, completely demineralized | ad 100.00% |
| of which DMEM/HAM's F-12 (1:1) | 0.5% |

The fatty phase which comprises the emulsifier is heated to 80° C., as is the water phase without the fraction which comprises the medium. At 80° C., both phases are combined, homogenized for about 3-10 minutes and then cooled to 48° C. or room temperature. Then, at a constant temperature of ±1° C., the water fraction is admixed with medium and mixed. The preparations below are prepared accordingly.

Example 3

| | |
|---|---|
| PEG-40 stearate | 1.00% |
| Glyceryl stearate | 2.00% |
| Cetyl alcohol | 3.00% |
| Mineral oil DAB 9 | 2.00% |
| Safflower oil | 2.00% |
| Isopropyl palmitate | 4.50% |
| Glycerol | 3.00% |
| Magnesium sulfate | 1.20% |
| Preservative | 0.50% |
| Water, completely demineralized | ad 100.00% |
| of which DMEM/HAM's F-12 (1:1) | 2.5% |

Example 4

| | |
|---|---|
| PEG-80 stearate | 2.00% |
| Cetyl alcohol | 3.00% |
| Mineral oil DAB 9 | 1.50% |
| Evening primrose oil | 2.50% |
| Isopropyl palmitate | 5.40% |
| Propylene glycol | 3.00% |
| Potassium chloride | 0.60% |
| Preservative | 0.50% |
| Water, completely demineralized | ad 100.00% |
| of which DMEM/HAM's F-12 (1:1) | 5% |

Example 5

| | |
|---|---|
| Steareth-100 | 2.00% |
| Myristyl alcohol | 1.00% |
| Mineral oil DAB 9 | 3.00% |
| Castor oil | 3.00% |
| Cyclomethicone | 2.00% |
| Propylene glycol | 3.00% |
| Glycerol | 5.00% |
| Potassium chloride | 3.00% |
| Preservative | 0.50% |
| Water, completely demineralized | ad 100.00% |
| of which MCDB 153 | 0.5% |

Example 6

| | |
|---|---|
| Steareth-20 | 2.00% |
| Cetearyl | 3.00% |
| Vaseline | 0.50% |
| Wheat germ oil | 1.50% |
| Dimethicone | 5.00% |
| Glycerol | 5.00% |
| Sodium chloride | 3.00% |
| Preservative | 0.50% |
| Water, completely demineralized | ad 100.00% |
| of which DMEM/HAM's F-12 (1:1) | 15% |

Example 6a

| | |
|---|---|
| Dimethicone copolyol | 2.00% |
| Cetearyl alcohol | 3.00% |
| Vaseline | 0.50% |
| Wheat germ oil | 1.50% |
| Dimethicone | 5.00% |
| Glycerol | 5.00% |
| Sodium chloride | 3.00% |
| Preservative | 0.50% |
| Water, completely demineralized | ad 100.00% |
| of which MCDB 153 | 1.5% |

Example 7

| | |
|---|---|
| PEG-20 behenate | 2.00% |
| Stearyl alcohol | 3.00% |
| Vaseline | 1.00% |
| Grape seed oil | 3.00% |
| Dimethicone | 3.00% |
| Sorbitol | 5.00% |
| Zinc sulfate | 3.00% |
| Preservative | 0.50% |
| Water, completely demineralized | ad 100.00% |
| of which MCDB 153 | 5% |

Example 7a

| | |
|---|---|
| Decaglyn 1-IS | 2.00% |
| Stearyl alcohol | 3.00% |
| Vaseline | 1.00% |
| Grape seed oil | 3.00% |
| Dimethicone | 3.00% |
| Sorbitol | 5.00% |
| Zinc sulfate | 3.00% |
| Preservative | 0.50% |
| Water, completely demineralized | ad 100.00% |
| of which MCDB 153 | 40% |

Example 8

| | |
|---|---|
| PEG-20 myristate | 2.00% |
| Stearyl alcohol | 3.00% |
| Vaseline | 2.00% |
| Castor oil | 5.00% |
| Dimethicone | 5.00% |
| Sorbitol | 5.00% |
| Zinc sulfate | 3.00% |
| Preservative | 0.50% |
| Water, completely demineralized | ad 100.00% |
| of which MCDB 153 | 0.1% |

Example 8a

| | |
|---|---|
| Sucrose laurate | 2.00% |
| Stearyl alcohol | 3.00% |
| Vaseline | 2.00% |
| Castor oil | 5.00% |
| Dimethicone | 5.00% |
| Sorbitol | 5.00% |
| Zinc sulfate | 3.00% |
| Preservative | 0.50% |
| Water, completely demineralized | ad 100.00% |
| of which MCDB 153 | 12% |

Example 9

| | |
|---|---|
| PEG-80 behenate | 2.00% |
| Glyceryl behenate | 4.00% |
| Squalane | 3.00% |
| Castor oil | 5.40% |
| Glycerol | 6.00% |
| Magnesium sulfate | 2.60% |
| Preservative | 0.50% |
| Water, completely demineralized | ad 100.00% |
| of which MCDB 153 | 8.5% |

Example 10

O/W Emulsion

| | % by weight |
|---|---|
| Glyceryl stearate citrate | 3.00 |
| Stearyl alcohol | 1.00 |
| Octyldodecanol | 1.00 |
| Caprylic/capric triglycerides | 1.00 |
| Dicaprylyl ether | 1.00 |
| Carbomer | 0.15 |
| Glycerol | 3.00 |
| Perfume, preservative, NaOH, dyes, antioxidants, etc. | q.s. |
| Water | ad 100.00 |
| of which DMEM/HAM's F-12 (1:1) | 2.5% |
| pH adjusted to | 5.5 |

Example 11

O/W Emulsion

| | % by weight |
|---|---|
| Glyceryl stearate citrate | 3.00 |
| Stearyl alcohol | 1.00 |
| Octyldodecanol | 0.25 |
| Caprylic/capric triglycerides | 0.25 |
| Dicaprylyl ether | 0.25 |
| Carbomer | 0.15 |
| Glycerol | 3.00 |
| Perfume, preservative, NaOH, dyes, antioxidants, etc. | qs |
| Water | ad 100.00 |
| of which MCDB 153 | 0.5% |
| pH adjusted to | 5.5 |

Example 12

O/W Emulsion

| | % by weight |
|---|---|
| Glyceryl stearate citrate | 3.00 |
| Behenyl alcohol | 1.00 |
| Dimethicone | 1.50 |
| Cyclomethicone | 1.50 |
| Carbomer | 0.15 |
| Glycerol | 6.00 |
| Perfume, preservative, NaOH, dyes, antioxidants, etc. | qs |
| Water | ad 100.00 |
| of which DMEM/HAM's F-12 (1:1) | 5% |
| pH adjusted to | 5.5 |

Example 13

O/W Emulsion

| | % by weight |
|---|---|
| Glyceryl stearate citrate | 3.00 |
| Stearyl alcohol | 1.00 |
| Octyldodecanol | 0.25 |
| Caprylic/capric triglycerides | 0.25 |
| Dicaprylyl ether | 0.25 |
| Dimethicone | 0.50 |
| Carbomer | 0.15 |
| Glycerol | 3.00 |
| Aluminum Starch Octenyl Succinate | 0.50 |
| Talc | 0.50 |
| Bentonite | 0.50 |
| Perfume, preservative, NaOH, dyes, antioxidants, etc. | q.s. |
| Water | ad 100.00 |
| of which MCDB 153 | 80% |
| pH adjusted to | 5.5 |

Example 14

O/W Emulsion

|  | % by weight |
| --- | --- |
| Glyceryl stearate citrate | 3.00 |
| Cetyl alcohol | 1.00 |
| Squalane | 1.00 |
| Jojoba oil | 1.00 |
| Paraffinum liquidum | 1.00 |
| Carbomer | 0.10 |
| Glycerol | 3.00 |
| Serine | 0.50 |
| Tocopherol acetate | 1.00 |
| Carbomer | 0.10 |
| Xanthan gum | 0.10 |
| Perfume, preservative, NaOH, dyes, antioxidants, etc. | q.s. |
| Water | ad 100.00 |
| of which MCDB 153 | 75.5% |
| pH adjusted to | 6.0 |

Example 15

O/W Emulsion

|  | % by weight |
| --- | --- |
| Glyceryl stearate citrate | 3.00 |
| Cetyl alcohol | 0.50 |
| Octyldodecanol | 0.40 |
| Caprylic/capric triglycerides | 0.40 |
| Dicaprylyl ether | 0.40 |
| Carbomer | 0.10 |
| Glycerol | 3.00 |
| Serine | 0.50% |
| Perfume, preservative, NaOH, dyes, antioxidants, etc. | q.s. |
| Water | ad 100.00 |
| of which MCDB 153 | 40% |
| pH adjusted to | 5.5 |

Example 16

Emulsion Make-Up

|  | % by weight |
| --- | --- |
| Glyceryl stearate citrate | 3.00 |
| Stearyl alcohol | 1.00 |
| Dimethicone | 0.50 |
| Glycerol | 1.50 |
| 1,3-Butylene glycol | 1.50 |
| Magnesium silicate | 1.00 |
| Mica | 1.00 |
| Iron oxides | 1.00 |
| Titanium dioxide | 2.50 |
| Talc | 5.00 |
| Carbomer | 0.15 |
| Perfume, preservative, NaOH, dyes, antioxidants, etc. | q.s. |
| Water | ad 100.00 |
| of which MCDB 153 | 20% |
| pH adjusted to | 5.5 |

This example shows the advantageous application according to the invention of a cosmetic preparation comprising skin cell culture medium. Since the preparation can be used as make-up, it allows the user, for example in the case of burn injuries, to conceal these cosmetically and at the same time the user makes a contribution to the regeneration and restoration of the injured skin without being externally visible.

Example 17

O/W Emulsion

|  | % by weight |
| --- | --- |
| Glyceryl stearate citrate | 3.00 |
| Stearyl alcohol | 1.00 |
| Octyldodecanol | 0.25 |
| Caprylic/capric triglycerides | 0.25 |
| Dicaprylyl ether | 0.25 |
| Octyl methoxycinnamate | 4.00 |
| Benzophenone-3 | 3.00 |
| Octyl salicylate | 3.00 |
| Carbomer | 0.15 |
| Glycerol | 3.00 |
| Perfume, preservative, NaOH, dyes, antioxidants, etc. | q.s. |
| Water | ad 100.00 |
| of which MCDB 153 | 40% |
| pH adjusted to | 5.5 |

Example 18

O/W Emulsion

|  | % by weight |
| --- | --- |
| Glyceryl stearate citrate | 3.00 |
| Stearyl alcohol | 1.00 |
| Octyldodecanol | 0.50 |
| Caprylic/capric triglycerides | 0.50 |
| Dicaprylyl ether | 0.50 |
| Distarch phosphate | 1.00 |
| Ethanol | 10.00 |
| Carbomer | 0.15 |
| Glycerol | 3.00 |
| Perfume, preservative, NaOH, dyes, antioxidants, etc. | q.s. |
| Water | ad 100.00 |
| of which MCDB 153 | 35% |
| pH adjusted to | 5.5 |

Example 19

Emulsifier Gel

| | % by weight |
|---|---|
| Glyceryl stearate citrate | 3.00 |
| Stearyl alcohol | 1.00 |
| Ethanol | 2.00 |
| Aluminum Starch Octenyl Succinate | 0.25 |
| Talc | 0.25 |
| Tapioca starch | 0.25 |
| Carbomer | 0.15 |
| Glycerol | 3.00 |
| Perfume, preservative, NaOH, dyes, antioxidants, etc. | q.s. |
| Water | ad 100.00 |
| of which DMEM/HAM's F-12 (1:1) | 3.5% |
| pH adjusted to | 5.5 |

What is claimed is:

1. A cosmetic or dermatological preparation, wherein the preparation is formulated as a cosmetic or dermatological preparation for application to skin, comprises one or more tissue culture media selected from HAM's F-10, HAM's F-12, DMEM, and MCDB, further comprises at least one substance selected from sunscreen filters, perfumes, dyes, pearlizing agents, and pigments having a coloring effect, and is present as one of an oil-in-water (O/W) emulsion, a water-in-oil (W/O) emulsion, a water-in-oil-in-water (W/O/W) emulsion, and a microemulsion.

2. The preparation of claim 1, wherein the preparation comprises one or more tissue culture media selected from HAM's F-10, HAM's F-12, and DMEM.

3. The preparation of claim 1, wherein the one or more tissue culture media are present in an amount of from 1% to 50% by weight, based on a total weight of the preparation.

4. The preparation of claim 1, wherein the one or more tissue culture media together comprise all of the following components in the following concentration ranges in mg/l:

| | | |
|---|---|---|
| Biotin | 0.0036 | 0.0146 |
| $CaCl_2 \cdot 2 H_2O$ | 4.41 | 116.61 |
| Calcium pantothenate | 0.25 | 2.24 |
| Choline chloride | 9 | 13.96 |
| $CuSO_4 \cdot 5 H_2O$ | 0.0002496 | 0.00125 |
| D-Glucose | 1081 | 3151 |
| $FeSO_4 \cdot 7 H_2O$ | 0.417 | 1.39 |
| Folic acid | 0.79 | 2.65 |
| Glycine | 7.51 | 18.75 |
| Inositol | 12.6 | 18.02 |
| KCl | 111.83 | 311.8 |
| L-Alanine | 4.5 | 8.91 |
| L-Arginine•HCl | 147.5 | 210.7 |
| L-Asparagine | 7.5 | 15.01 |
| L-Aspartic acid | 3.99 | 6.65 |
| L-Cysteine•HCl | 15.75 | 42.04 |
| L-Glutamine | 365.3 | 877.2 |
| L-Glutamic acid | 7.35 | 14.71 |
| L-Histidine•HCl•$H_2O$ | 16.77 | 31.5 |
| Lipoic acid | 0.11 | 0.2063 |
| L-Isoleucine | 1.968 | 54.5 |
| L-Leucine | 59 | 65.6 |
| L-Lysine•HCl | 18.27 | 91.25 |
| L-Methionine | 4.475 | 17.24 |
| L-Phenylalanine | 4.956 | 35.5 |
| L-Proline | 17.25 | 34.53 |
| L-Serine | 26.25 | 63.06 |
| L-Threonine | 11.91 | 53.5 |
| L-Tyrosine | 2.718 | 38.7 |
| L-Valine | 35.13 | 52.85 |
| $MgCl_2 \cdot 6 H_2O$ | 61 | 122 |
| $Na_2HPO_4 \cdot 7 H_2O$ | 71 | 536.2 |
| NaCl | 6999.5 | 7599 |
| $NaHCO_3$ | 1176 | 2438 |
| Sodium pyruvate | 47 | 63 |
| Nicotinamide | 0.03663 | 2.02 |
| Pyridoxine HCl | 0.031 | 0.06171 |
| Riboflavin | 0.03764 | 0.22 |
| Thiamine HCl | 0.3373 | 2.17 |
| Thymidine | 0.37 | 0.7266 |
| Vitamin $B_{12}$ (cobalamine) | 0.68 | 4.07. |

5. The preparation of claim 1, wherein the one or more tissue culture media comprise DMEM/HAM's F-12 (1:1).

6. The preparation of claim 1, which further comprises a mixture comprising collagen, chitosan having a degree of acetylation of up to 50% and glycosylaminoglycan.

7. The preparation of claim 1, which further comprises one or more serum substitutes.

8. The preparation of claim 7 wherein the one or more serum substitutes function as osmoregulators.

9. The preparation of claim 7, wherein the one or more serum substitutes comprise one or more of chitosan, chrondroitin-6-sulfate and collagen.

10. The preparation of claim 1, which further comprises glutamine.

11. The preparation of claim 1, wherein ratios of ingredients of the one or more cell culture media of mineral and organic biofactors are suitable for the retention, the cultivation and the care of skin cells at least one of in vitro, ex vivo and in vivo.

12. The preparation of claim 1, wherein the preparation is present as at least one of a spray, a foam, a foam aerosol, an ointment and a cosmetic stick preparation.

13. The preparation of claim 1, wherein the preparation is present as a O/W emulsion.

14. The preparation of claim 1, wherein the preparation is present as a W/O emulsion.

15. The preparation of claim 1, wherein the preparation is present as a W/O/W emulsion.

16. The preparation of claim 1, wherein the preparation is present as a microemulsion.

17. The preparation of claim 1, wherein the preparation is associated with instructions directing its use in a cosmetic application.

18. A process for making the preparation of claim 1, wherein the process comprises mixing the one or more tissue culture media with one or more other cosmetic constituents of the preparation immediately prior to use.

19. The preparation of claim 1, wherein the preparation is serum-free.

20. A cosmetic or dermatological preparation, wherein the preparation is formulated as a cosmetic or dermatological preparation for application to skin and comprises one or more tissue culture media, a membrane system, and at least one substance selected from sunscreen filters, perfumes, dyes, pearlizing agents, and pigments having a coloring effect.

21. The preparation of claim 20, wherein the membrane system comprises a liposome.

22. The preparation of claim 20, wherein the membrane system comprises a cyclodextrin.

23. A cosmetic or dermatological preparation, wherein the preparation is formulated as a cosmetic or dermatological preparation for application to skin and comprises one or more tissue culture media and a chitosan/collagen/condroitin 6-sulfate sponge.

24. The preparation of claim 23, wherein the one or more tissue culture media comprise one or more skin cell culture media.

25. The preparation of claim 24, wherein the one or more tissue culture media are serum-free.

26. The preparation of claim 23, which further comprises glutamine.

27. The preparation of claim 23, wherein the preparation further comprises at least one substance selected from sunscreen filters, perfumes, dyes, pearlizing agents, and pigments with a coloring effect.

28. A cosmetic or dermatological preparation, wherein the preparation is formulated as a cosmetic or dermatological preparation for application to skin and comprises one or more tissue culture media selected from HAM's F-10, HAM's F-12, DMEM, and MCDB and at least one substance selected from perfumes, and pearlizing agents.

29. The preparation of claim 28, wherein the preparation is present as at least one of an aqueous or aqueous-alcoholic solution, a spray, a foam, a foam aerosol, an ointment, an aqueous gel and a cosmetic stick preparation.

30. The preparation of claim 28, wherein the preparation further comprises glutamine.

31. The preparation of claim 28, wherein the preparation is associated with instructions directing its use in a cosmetic application.

32. A cosmetic or dermatological preparation, wherein the preparation is formulated as a cosmetic or dermatological preparation for application to skin, comprises one or more tissue culture media selected from HAM's F-10, HAM's F-12, DMEM, and MCDB, further comprises a mixture comprising collagen, chitosan having a degree of acetylation of up to 50%, and glycosylaminoglycan, is serum-free, and is present as one of an oil-in-water (O/W) emulsion, a water-in-oil (W/O) emulsion, a water-in-oil-in-water (W/O/W) emulsion, and a microemulsion.

33. The preparation of claim 32, which further comprises glutamine.

34. The preparation of claim 32, wherein the preparation is present as at least one of a spray, a foam, a foam aerosol, an ointment, and a cosmetic stick preparation.

35. A cosmetic or dermatological preparation, wherein the preparation is formulated as a cosmetic or dermatological preparation for application to skin, comprises one or more tissue culture media, at least one of a polyurethane matrix and a chitosan/collagen/condroitin 6-sulfate sponge, and at least one substance selected from sunscreen filters, perfumes, dyes, pearlizing agents, and pigments having a coloring effect.

36. The preparation of claim 35, wherein the one or more tissue culture media comprise one or more skin cell culture media.

37. The preparation of claim 35, wherein the one or more tissue culture media are serum-free.

38. The preparation of claim 35, which further comprises glutamine.

* * * * *